(12) United States Patent
Cannell et al.

(10) Patent No.: US 7,459,150 B2
(45) Date of Patent: *Dec. 2, 2008

(54) HEAT ACTIVATED DURABLE CONDITIONING COMPOSITIONS COMPRISING AN AMINATED C5 TO C7 SACCHARIDE UNIT AND METHODS FOR USING SAME

(75) Inventors: David W. Cannell, Plainfield, NJ (US); Hitendra Mathur, Woodbridge, NJ (US); Nghi Van Nguyen, Edison, NJ (US)

(73) Assignee: L'Oréal S.A., Paris (FR)

( * ) Notice: Subject to any disclaimer, the term of this patent is extended or adjusted under 35 U.S.C. 154(b) by 375 days.

This patent is subject to a terminal disclaimer.

(21) Appl. No.: 09/820,858

(22) Filed: Mar. 30, 2001

(65) Prior Publication Data

US 2002/0172653 A1 Nov. 21, 2002

(51) Int. Cl.
- A61K 8/73 (2006.01)
- A61K 31/715 (2006.01)
- A61Q 5/00 (2006.01)
- A61Q 5/12 (2006.01)
- C11D 1/62 (2006.01)

(52) U.S. Cl. .............. 424/70.13; 424/70.1; 424/70.28; 424/70.12; 424/70.122; 424/70.11; 424/70.22; 424/70.31; 424/70.27; 424/70.21; 514/54

(58) Field of Classification Search .............. 424/70.13, 424/70.28, 70.1, 70.12, 70.122, 70.11, 70.22, 424/70.31, 70.27, 70.21; 514/55
See application file for complete search history.

(56) References Cited

U.S. PATENT DOCUMENTS

| | | | | |
|---|---|---|---|---|
| 4,743,442 | A | * | 5/1988 | Raaf et al. ............... 424/47 |
| 4,767,463 | A | * | 8/1988 | Brode et al. ............. 106/162.2 |
| 4,900,545 | A | | 2/1990 | Wisotzki et al. |
| 4,913,743 | A | * | 4/1990 | Brode et al. ............. 106/162.2 |
| 5,332,581 | A | * | 7/1994 | Yoshihara et al. ......... 424/70.1 |
| 5,348,737 | A | | 9/1994 | Syed et al. |
| 5,494,533 | A | * | 2/1996 | Woodin et al. ............. 134/40 |
| 5,597,811 | A | * | 1/1997 | Gruber ..................... 514/55 |
| 5,641,477 | A | | 6/1997 | Syed et al. |
| 5,660,838 | A | | 8/1997 | Koga et al. |
| 5,888,951 | A | | 3/1999 | Gagnebien et al. |
| 5,962,015 | A | * | 10/1999 | Delrieu et al. ............. 424/450 |
| 5,993,792 | A | * | 11/1999 | Rath et al. ............... 424/70.28 |
| 6,486,105 | B1 | * | 11/2002 | Cannell et al. ............. 510/124 |
| 2002/0102228 | A1 | * | 8/2002 | Dunlop et al. ............. 424/70.1 |

FOREIGN PATENT DOCUMENTS

| | | |
|---|---|---|
| DE | 297 09 853 | 11/1998 |
| JP | 04-266812 | 9/1992 |
| JP | 06-122614 | 5/1994 |
| JP | 09-059134 | 5/1997 |
| JP | 10-279439 | 10/1998 |

OTHER PUBLICATIONS

Milczarek et al., "The Mechanism and Stability of Thermal Transitions in Hair Keratin", *Colloid and Polymer Science*, vol. 270, No. 11, 1992, pp. 1106-1115.
Hollenberg et al., "Möglichkeiten Zur Beeinflussung Der Haarstruktur Durch Pflegeprodukte", *SÖFW-Journal*, vol. 121, No. 2, 1995, pp. 82-89.
ACS Abstract 123:296216 CA: Hollenberg et al., *SÖFW-Journal*, vol. 121, No. 2, 1995, pp. 82-89.
Hollenberg et al., "Möglichkeiten Zur Beeinflussung Der Haarstruktur Mit Kosmetischen Mittein", *Seifen—Öle—Fette—Wachse*, vol. 117, Jan. 1991, pp. 9-18.
ACS Abstract 114:149908 CA: Hollenberg et al., *Seifen-Öle—Fette—Wachse*, vol. 117, Jan. 1991, pp. 9-18.
Spei et al., "Thermoanalytical Investigations of Extended and Annealed Keratins", *Colloid & Polymer Science*, vol. 265, No. 11, 1987, pp. 965-970.
Sandhu et al., "A Simple and Sensitive Technique, Based on Protein Loss Measurements, to Assess Surface Damage to Human Hair", *J. Soc. Cosmet. Chem*, vol. 44, No. 3, May/Jun. 1993, pp. 163-175.
Results from literature search performed by Assignee, 11 pages.
Results from literature search performed by Assignee, 24 pages.
English language Derwent Abstract of DE 297 09 853, Sep. 20, 1994.
English language Derwent Abstract of JP 06-122614, May 6, 1994.
English language Derwent Abstract of JP 04-266812, Sep. 22, 1992.
English language Derwent Abstract of JP 10-279439, Oct. 20, 1998.
English language Derwent Abstract of JP 09-059134, Mar. 4, 1997.

\* cited by examiner

*Primary Examiner*—Michael G. Hartley
*Assistant Examiner*—Blessing M Fubara
(74) *Attorney, Agent, or Firm*—Finnegan, Henderson, Farabow, Garrett, & Dunner, LLP

(57) ABSTRACT

Compositions, optionally heat activated, methods, and kits for caring for, treating or durable conditioning of at least one keratinous fiber comprising at least one compound comprising at least two quaternary ammonium groups; and at least one compound comprising at least one $C_5$ to $C_7$ saccharide unit substituted with at least one amino group; and heating the at least one keratinous fiber.

138 Claims, No Drawings

HEAT ACTIVATED DURABLE CONDITIONING COMPOSITIONS COMPRISING AN AMINATED C5 TO C7 SACCHARIDE UNIT AND METHODS FOR USING SAME

The present invention relates to compositions, kits comprising these compositions, and methods for using these compositions for care, treatment or durable conditioning of at least one keratinous fiber, including human keratinous fibers, comprising (i) at least one compound comprising at least two quaternary ammonium groups, and (ii) at least one compound comprising at least one $C_5$ to $C_7$ saccharide unit substituted with at least one amino group, which is different from said at least one compound comprising at least two quaternary ammonium groups. These compositions may be used to care for, treat and/or durably condition at least one keratinous fiber.

Shampoos generally comprise surfactants, such as anionic surfactants, to clean the hair. It is known that anionic surfactants not only remove the dirt and soil but also remove the naturally-present sebum from hair. Thus, shampoos may leave the hair dull and dry, that is, with what is known in the art as "creak". This generally makes the hair extremely difficult to comb either wet or dry, and once dry, the hair may not be amenable to styling, and may have undesirable electrostatic properties, causing the hair to "fly away." Due to the unsatisfactory condition of shampooed hair, many consumers use a conditioning composition to improve at least one of these undesirable characteristics.

Conditioning agents in the prior art include cationic compounds such as cationic surfactants and cationic polymers which may render the hair more manageable, at least temporarily. For example, quaternized ammonium compounds may be used as hair conditioning agents. These compounds may be substantive to the hair due to the ionic interaction between their positive charge on the ammonium nitrogen atom and negative charges on the surface of the hair fibers. This ionic interaction, in effect, allows the conditioning agents to coat the hair shaft and thereby prevent tangling and matting of the individual hair fibers. Thus, the ability of these cationic compounds to adsorb to and/or react with the keratinous material of the hair makes them desirable compounds for conditioning the hair, such as for detangling wet hair and imparting manageability to dry hair.

Conditioning agents may be comprised in a composition distinct from the shampoo composition or may be incorporated into the shampoo composition itself. For example, quaternized ammonium compounds have been included in compositions such as shampoos, conditioners and treatments that are normally applied to hair at room temperature. However, the effect of these conditioning agents may not be long lasting. Normally, because of the weak ionic bond between the quaternized ammonium compounds and the hair fiber, the quaternized ammonium compounds are washed off the hair easily. This is especially true during shampooing, wherein anionic surfactants are present, generally in high concentrations. In such a case, the anionic surfactants in the shampoo and the cationic conditioning agents are known to form a complex which may be easily removed from the hair during the shampooing and/or which decreases the cleansing capabilities of the anionic surfactant and the conditioning capabilities of the conditioning agent.

Accordingly, in practice, most consumers prefer to apply, at room temperature, an anionic surfactant-based shampoo to cleanse the hair, then rinse the hair, follow rinsing by application of a conditioner composition including a cationic compound to condition the hair, then rinse the hair again. As discussed above, this may only lead to temporary conditioning of the hair, as the next shampoo may remove the majority of the conditioning agents from the hair. Thus, there is a need for compositions and methods that impart a durable conditioning to the hair.

Sugars and sugar derivatives are one class of the countless number of compounds that have been added to hair care compositions. Documented uses of sugars in hair care compositions include: the use of glucose to improve tke tactile and elastic properties of natural hair (Hollenberg and Mueller, *SOFW J.* 121(2) (1995)); the use of glucose for hair damage prophylaxis and damaged hair repair (Hollenberg & Matzik, Seifen, Oele, Fette, Wachase 117(1) (1991)); the use of glucose in shampoos (J04266812, assigned to Lion Corp.); the use of trehalose for moisture retention (J06122614, assigned to Shiseido Co. Ltd.); a composition for the lanthionization of hair comprising a sugar (U.S. Pat. Nos. 5,348,737 and 5,641,477, assigned to Avlon Ind. Inc.); the incorporation of xylobiose into cosmetic compositions to provide enhanced moisture retention and reduce excessive roughness and dryness of the skin and hair (U.S. Pat. No. 5,660,838, assigned to Suntory Ltd.); a composition for the regeneration of hair split-ends that contains at least one mono- or di-saccharide (U.S. Pat. No. 4,900,545, assigned to Henkel); hair care compositions to improve hair strength, hold and volume that contain C5 to C6 carbohydrates such as glucose; the use of fucose in a hair treatment to prevent split ends (DE29709853, assigned to Goldwell GMBH); and the use of saccharides in a shampoo to improve combing properties and control hair damage (J09059134, assigned to Mikuchi Sangyo K K).

In essence, sugars have been applied to hair for countless reasons from moisturizing to enhancing hair growth (J10279439, assigned to Kureha Chem. Ind. Co. Ltd.). Clearly, however, not all sugars are the same and not all sugars impart the same properties when applied to a keratinous fiber.

The inventors have envisaged the application to at least one keratinous fiber of at least one composition comprising at least one compound comprising at least two quaternary ammonium groups and at least one compound comprising at least one $C_5$ to $C_7$ saccharide unit substituted with at least one amino group. In particular, the inventors have discovered that such compositions and methods using these compositions comprising applying them to at least one keratinous fiber and heating the at least one keratinous fiber impart a durable conditioning to the at least one keratinous fiber. The compositions of the invention may also be used to care for, or treat, the at least one keratinous fiber.

Thus, to achieve at least one of these and other advantages, the present invention, in one aspect, provides a composition for durable conditioning of at least one keratinous fiber comprising at least one compound comprising at least two quaternary ammonium groups and at least one compound comprising at least one $C_5$ to $C_7$ saccharide unit substituted with at least one amino group, wherein the at least one compound and at least one sugar are present in an amount effective to durably condition the at least one keratinous fiber. In one embodiment, the composition is heat-activated.

In another embodiment, the present invention is drawn to a method for caring for or treating at least one keratinous fiber comprising applying to the at least one keratinous fiber at least one compound comprising at least two quaternary ammonium groups and at least one compound comprising at least one $C_5$ to $C_7$ saccharide unit substituted with at least one amino group, and heating the at least one keratinous fiber, wherein the at least one sugar and at least one compound are present in an amount effective to care for or treat the at least one keratinous fiber, and further wherein the composition is applied prior to or during heating.

In another embodiment, the present invention is drawn to a method for durable conditioning of at least one keratinous fiber comprising applying to the at least one keratinous fiber at least one compound comprising at least two quaternary ammonium groups and at least one compound comprising at least one $C_5$ to $C_7$ saccharide unit substituted with at least one amino group, and heating the at least one keratinous fiber, wherein the at least one sugar and at least one compound are present in an amount effective to durably condition the at least one keratinous fiber, and further wherein the composition is applied prior to or during heating.

In yet another embodiment, the present invention provides a kit for caring for, treating or durably conditioning comprising at least two compartments, wherein a first compartment comprises a first composition comprising at least one compound comprising at least two quaternary ammonium groups, and wherein a second compartment comprises a second composition comprising at least one compound comprising at least one $C_5$ to $C_7$ saccharide unit substituted with at least one amino group. In one embodiment, at least one compartment comprises at least one additional sugar, different from the at least one compound comprising at least one $C_5$ to $C_7$ saccharide unit substituted with at least one amino group.

Certain terms used herein are defined below:

"At least one" as used herein means one or more and thus includes individual components as well as mixtures/combinations.

"Conditioning" as used herein means imparting at least one of combability, manageability, moisture-retentivity, luster, shine, softness, and body to the hair.

"Durable conditioning" as used herein means that, following at least six shampoos after treatment, treated hair still remains in a more conditioned state as compared to untreated hair. The state of conditioning can be evaluated by measuring, and comparing, the ease of combability of the treated hair and of the untreated hair in terms of combing work (gm-in) and/or the substantivity of the conditioning agent on the hair (for example, see Example).

"Heating" refers to the use of elevated temperature (i.e., above 100° C.). In one embodiment, the heating in the inventive method may be provided by directly contacting the at least one keratinous fiber with a heat source, e.g., by heat styling of the at least one keratinous fiber. Non-limiting examples of heat styling by direct contact with the at least one keratinous fiber include flat ironing, and curling methods using elevated temperatures (such as, for example, setting hair in curlers and heating, and curling with a curling iron and/or hot rollers). In another embodiment, the heating in the inventive method may be provided by heating the at least one keratinous fiber with a heat source which may not directly contact the at least one keratinous fiber. Non-limiting examples of heat sources which may not directly contact the at least one keratinous fiber include blow dryers, hood dryers, heating caps and steamers.

"A heat-activated" composition, as used herein, refers to a composition which, for example, conditions the at least one keratinous fiber quantitatively better than the same composition which is not heated during or after application of the composition. Another example includes a composition which cares for or treats at least one keratinous fiber quantitatively better than the same composition which is not heated during or after application.

"Keratinous fibers" as defined herein may be human keratinous fibers, and may be chosen from, for example, hair.

"Oligosaccharides" as defined herein refers to compounds generally comprising from two to ten monosaccharide units, which may be identical or different, bonded together.

"Polysaccharides" as defined herein refers to compounds generally comprising greater than ten monosaccharide units, which may be identical or different, bonded together.

"Polymers" as defined herein comprise copolymers (including terpolymers) and homopolymers. Further, the term "polymers" comprises both oligosaccharides and polysaccharides.

"Quaternary ammonium groups" as defined herein refers to both ammonium groups that are quaternized and to amine groups which are capable of being quaternized (such as appended amines).

It is to be understood that both the foregoing general description and the following detailed description are exemplary and explanatory only and are not restrictive of the invention, as claimed. Reference will now be made in detail to exemplary embodiments of the present invention.

As described above, sugars have been used in hair care compositions and other treatments for their moisture retaining properties. However, it was unexpectedly discovered by the present inventors that, in addition to retaining moisture, a certain class of compounds comprising at least one $C_5$ to $C_7$ saccharide unit substituted with at least one amino group had other properties that made them particularly desirable for use on keratinous fibers. In particular with respect to hair, compositions comprising at least one compound comprising at least two quaternary ammonium groups and at least one compound comprising at least one $C_5$ to $C_7$ saccharide unit substituted with at least one amino group (different from said at least one compound comprising at least two quaternary ammonium groups) were found to durably condition the hair and also found to be useful in caring for and treating the hair. Further, these compositions may impart to the at least one keratinous fiber a durable conditioning even after shampooing the at least one keratinous fiber subsequent to treatment with a composition comprising at least one such compound. This is particularly true when the compositions are applied to the hair, and the hair is then heated.

Thus, the invention provides compositions for durable conditioning of at least one keratinous fiber comprising (i) at leeast one compound comprising at least two quaternary ammonium groups and (ii) at least one compound comprising at least one $C_5$ to $C_7$ saccharide unit substituted with at least one amino group, wherein the at least one compound comprising at least two quaternary ammonium groups and at least one compound comprising at least one $C_5$ to $C_7$ saccharide unit substituted with at least one amino group are present in an amount effective to condition the at least one keratinous fiber. In one embodiment, the composition is heat-activated. The composition may further comprise at least one additional sugar.

The present invention also provides methods for caring for or treating at least one keratinous fiber comprising applying to the at least one keratinous fiber a composition comprising (i) at least one compound comprising at least two quaternary ammonium groups, and (ii) at least one compound comprising at least one $C_5$ to $C_7$ saccharide unit substituted with at least one amino group, and heating the at least one keratinous fiber. The composition may be applied prior to or during heating. Further, the at least one compound comprising at least two quaternary ammonium groups and the at least one compound comprising at least one $C_5$ to $C_7$ saccharide unit substituted with at least one amino group are present in an amount effective to care for or treat the at least one keratinous fiber, depending on the embodiment. In one embodiment, the composition both cares for and treats the at least one keratinous fiber. The composition may further comprise at least one additional sugar.

The present invention also provides methods for durable conditioning of at least one keratinous fiber comprising applying to the at least one keratinous fiber a composition comprising (i) at least one compound comprising at least two quaternary ammonium groups, and (ii) at least one compound comprising at least one $C_5$ to $C_7$ saccharide unit substituted with at least one amino group, and heating the at least one keratinous fiber. The composition may be applied prior to or during heating. Further, the at least one compound comprising at least two quaternary ammonium groups and the at least one compound comprising at least one $C_5$ to $C_7$ saccharide unit substituted with at least one amino group are present in an amount effective to durably condition the at least one keratinous fiber, depending on the embodiment. The composition may further comprise at least one additional sugar.

According to the present invention, the at least one compound comprising at least two quaternary ammonium groups may be chosen from water soluble compounds, oil soluble compounds, and compounds soluble in organic solvents. Non-limiting examples of the at least one film forming agent are those listed at pages 1703 to 1706 of the CTFA International Cosmetic Ingredient Dictionary, $8^{th}$ edition (2000).

According to the present invention, the at least two quaternary ammonium groups may be identical or different. Amine groups which are capable of being quaternized may be chosen from primary, secondary, and tertiary amines. For example, the at least two quaternary ammonium groups may be chosen from substituent ammonium groups (such as terminal ammonium groups and pendant ammonium groups), substituent amino groups capable of being quaternized (such as terminal amino groups capable of being quaternized and pendant amino groups capable of being quaternized), ammonium groups forming part of the skeleton of at least one compound and amino groups capable of being quaternized forming part of the skeleton of at least one compound.

Thus, the at least one compound comprising at least two quaternary ammonium groups may be chosen from, for example, polymers comprising at least two quaternary ammonium groups derived from (i) at least one monomer unit comprising at least two quaternary ammonium groups as defined herein, and, optionally, (ii) at least one additional monomer unit different from the at least one monomer (i); and polymers comprising at least two quaternary ammonium groups derived from (i) at least one monomer comprising at least one quaternary ammonium group as defined herein, and, optionally, (ii) at least one additional monomer unit different from the at least one monomer (i). According to the present invention, the at least one additional monomer different from the at least one monomer (i) may or may not comprise at least one quaternary ammonium group as defined herein.

Non-limiting examples of monomers comprising at least one quaternary ammonium group as defined herein are vinyl monomers substituted with at least one group chosen from dialkylaminoalkyl acrylate, dialkylaminoalkyl methacrylate, monoalkylaminoalkyl acrylate, monoalkylaminoalkyl methacrylate, trialkyl methacryloxyalkyl ammonium salts, trialkyl acryloxyalkyl ammonium salts and diallyl quaternary ammonium salts; and vinyl quaternary ammonium monomers comprising at least one cyclic cationic nitrogen-containing ring (such as a pyridinium ring, an imidazolium ring, and a quaternized pyrrolidone ring).

Non-limiting examples of the at least one compound comprising at least two quaternary ammonium groups are copolymers derived from (i) vinyl monomers comprising at least one quaternary ammonium group as defined herein and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol. For example, the at least one compound comprising at least two quaternary ammonium groups may be chosen from copolymers derived from (i) 1-vinyl-2-pyrrolidone and (ii) 1-vinyl-3-methylimidazolium salt (CTFA designation; polyquaternium-16), which is commercially available from BASF Corporation under the LUVIQUAT tradename (e.g., LUVIQUAT FC 370) and copolymers derived from (i) 1-vinyl-2-pyrrolidone and (ii) dimethylaminoethyl methacrylate, (CTFA designation: polyquaternium-11), which is commercially available from Gaf Corporation (Wayne, N.J., USA) under the GAFQUAT tradename (e.g., GAFQUAT 755N). Further non-limiting examples of the at least one compound comprising at least two ammonium groups are optionally quaternized poly(vinylamine), which can be made by polymerizing vinylamine and optionally quaternizing, optionally quaternized poly-4-vinyl pyridine and optionally quaternized poly(ethyleneimine), which can be prepared by polymerizing ethyleneimine and optionally quaternizing.

According to the present invention, monomers comprising amine groups which are capable of being quaternized may be polymerized and then, optionally, converted to ammonium by a quaternization reaction, and/or may be quaternized prior to polymerization. For example, tertiary amine groups which are capable of being quaternized can be quaternized by reaction with a salt of the formula R'X wherein R' is a short chain alkyl, and X is an anion which forms a water soluble salt with the quaternized ammonium.

Further non-limiting examples of the at least one compound comprising at least two quaternary ammonium groups are cationic diallyl quaternary ammonium-comprising polymers such as dimethyldiallylammonium chloride homopolymer (CTFA designation: polyquaternium-6), copolymers derived from (i) acrylamide and (ii) dimethyldiallylammonium chloride (CTFA designation: polyquaternium-7); copolymers derived from (i) dimethyidiallylammonium chloride and (ii) sodium acrylate (CTFA designation: Polyquaternium-22); and terpolymers derived from (i) dimethyidiallylammonium chloride, (ii) acrylic amide and (iii) sodium acrylate (CTFA designation: Polyquaternium-39).

Other non-limiting examples of the at least one compound comprising at least two quaternary ammonium groups are derivatives of polysaccharide polymers such as cationic cellulose derivatives include cationic cellulose, which is available from Amerchol Corp. (Edison, N.J., USA) in their Polymer JR™, LR™ and SR™ series of polymers as salts of hydroxyethyl cellulose reacted with trimethyl ammonium substituted epoxide (CTFA designation: polyquaternium-10), and polymeric quaternary ammonium salts of hydroxyethyl cellulose reacted with lauryl dimethyl ammonium-substituted epoxide (CTFA designation: polyquaternium-24), which is available under the tradename Polymer LM-200™. Other non-limiting examples of cationic cellulose derivatives include cationic starch derivatives such as quaternary starch, which is available from Croda); cationic guar gum derivatives (such as guar hydroxypropyltrimonium chloride, which is available from Celanese Corp. in their Jaguar R series); and quaternary nitrogen-containing cellulose ethers.

Finally, further non-limiting examples of the at least one compound comprising at least two quaternary ammonium groups are silicone polymers comprising at least two quaternary ammonium groups. For example, the silicone polymers may be chosen from silicone polymers comprising at least two quaternary ammonium groups wherein the at least two quaternary ammonium groups may be terminal, pendant and/or form part of the polymeric skeleton. Non-limiting examples of such silicone polymers are amodimethicone which is sold by Dow-Corning Corp. in the form of its aqueous cationic emulsion under the trade name Silicone Emulsion No. 929 (a cationic aqueous emulsion emulsified with a cationic surfactant such as a long chain fatty acid quaternary ammonium compound such as stearalkonium chloride or tallowtrimonium chloride, and generally also an emulsifying assistant such as an ethoxylated alkyl phenol, for example, nonoxynol-10), and amino functional silicone polymers sold by Dow-Corning Corp. under the trade name Q4-656.

In one embodiment, the at least one compound comprising at least two quaternary ammonium groups is polyquaternium-10. In another embodiment, the at least one compound comprising at least two quaternary ammonium groups is polyquaternium-22, while in another embodiment, the at least one compound comprising at least two quaternary ammonium groups is polyethyleneimine. In yet another embodiment, the at least one compound comprising at least two quaternary ammonium groups is quaternized starch.

In one embodiment, the at least one compound comprising at least two quaternary ammonium groups further comprises at least one counterion. According to the present invention, any anionic counterions may be used for the at least two quaternary ammonium groups. Non-limiting examples of counterions are halide ions, sulfate ions, and methylsulfate ions, acetate ions, tosylate ions and phosphate ions.

The at least one compound comprising at least two quaternary ammonium groups of the present invention may be present in an amount generally ranging from 0.01% to 10% of active material by weight relative to the total weight of the composition, such as from 0.1% to 0.5% of active material by weight. One of ordinary skill in the art will recognize that the at least one compound according to the present invention may be commercially available, and may come from suppliers in the form of a dilute solution. The amounts of the at least one compound disclosed herein therefore reflect the weight percent of active material. Further, one of skill in the art will recognize that the charge density of the at least one compound will be dependent on the pH and the isoelectric point of the at least two quaternary ammonium groups.

The at least one $C_5$ to $C_7$ saccharide unit according to the present invention may be chosen from any pentose, hexose and heptose. Further, the at least one $C_5$ to $C_7$ saccharide unit can be chosen from their D-form, L-form and mixtures of any of the foregoing. Non-limiting examples of $C_5$ to $C_7$ saccharide units are aldopentoses (such as xylose, arabinose, lyxose, and ribose), ketopentoses (such as ribulose and xylulose), aldohexoses (such as glucose and galactose), ketohexoses (such as fructose and sorbose), and heptoses (such as aldoheptoses and ketoheptoses, e.g., galactoheptulose and glucoheptulose). The at least one $C_5$ to $C_7$ saccharide unit may be chosen from those comprising aldehyde groups (aldoses), furanoses and other ring structures. The at least one $C_5$ to $C_7$ saccharide unit may be further substituted with at least one group different from the at least one amino group.

Derivatives of $C_5$ to $C_7$ saccharide units may also be used as the at least one $C_5$ to $C_7$ saccharide unit in the present invention. For example, ammonias or primary amines may react with the aldehyde or ketone group of a saccharide unit to form an imine derivative (i.e., a compound containing the functional group C=N). These imine compounds are sometimes also referred to as Schiff bases. Other non-limiting examples of derivatives of $C_5$ to $C_7$ saccharide units are hemiacetal derivatives of $C_5$ to $C_7$ saccharide units, hemiketal derivatives of $C_5$ to $C_7$ saccharide units and any oxidized derivatives of $C_5$ to $C_7$ saccharide units. These derivatives may be formed, for example, from the reaction of the aldehyde or ketone group of a saccharide unit with an alcohol. As previously mentioned, the at least one $C_5$ to $C_7$ saccharide unit may be further substituted with at least one group different from the at least one amino group. Thus, in one embodiment, the derivatives of $C_5$ to $C_7$ saccharide units may be further substituted with at least one group different from the at least one amino group.

According to the present invention, the at least one amino group may be chosen from substituted and unsubstituted amino groups. For example, the at least one amino group may be chosen from N-acetyl amino groups.

Further, the at least one $C_5$ to $C_7$ saccharide unit may be substituted with the at least one amino group at any position on the saccharide unit. For example, in one embodiment, the at least one $C_5$ to $C_7$ saccharide unit is substituted with the at least one amino group at the C1 position of the at least one $C_5$ to $C_7$ saccharide unit. In another embodiment, the at least one $C_5$ to $C_7$ saccharide unit is substituted with the at least one amino group at the C2 position of the at least one $C_5$ to $C_7$ saccharide unit.

Non-limiting examples of the at least one compound include $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group. In one embodiment, the at least one compound is chosen from oligosaccharides derived from the at least one $C_5$ to $C_7$ saccharide unit substituted with at least one amino group.

Non-limiting examples of $C_5$ monosaccharides substituted with at least one amino group are pentosamines. In one embodiment, the pentosamines are chosen from aldopentosamines and ketopentosamines (such as xylosamine, arabinosamine, lyxosamine, ribosamine, ribulosamine and xylulosamine).

Non-limiting examples of $C_6$ monosaccharides substituted with at least one amino group include hexosamines (such as aldohexosamines and ketohexosamines). In one embodiment, for example, the hexosamines are chosen from glucosamine, galactosamine, allosamine, altrosamine, mannosamine, gulosamine, idosamine, galactosamine, and talosamine. In another embodiment, the at least one compound is glucosamine, and in another embodiment, is galactosamine.

Non-limiting examples of $C_7$ monosaccharides substituted with at least one amino group are heptosamines. For example, heptosamines may be chosen from aldoheptosamines and ketoheptosamines.

According to the present invention, the at least one compound comprising at least one $C_5$ to $C_7$ saccharide unit substituted with at least one amino group is present in the composition in an amount generally ranging from 0.01% to 10% by weight relative to the total weight of the composition, such as from 0.1% to 5% by weight.

The compositions of the present invention and those used in the methods of the present invention may further comprise at least one additional sugar which is different from the at least one compound comprising at least one $C_5$ to $C_7$ saccharide unit substituted with at least one amino group. The at least one additional sugar may, for example, aid in moisture retention. The effectiveness of a sugar in aiding in moisture retention may be measured by monitoring a DSC peak at a temperature ranging from 75° C. to 200° C.

The at least one additional sugar may be chosen from any sugar, carbohydrate or carbohydrate moiety. Non-limiting examples of the at least one additional sugar are monosaccharides, which include, but are not limited to, three to seven carbon sugars such as pentoses (for example, ribose, arabinose, xylose, lyxose, ribulose, and xylulose) and hexoses (for example, allose, altrose, glucose, mannose, gulose, idose, galactose, talose, sorbose, psicose, fructose, and tagatose); oligosaccharides such as disaccharides (such as maltose, sucrose, cellobiose, trehalose and lactose); and polysaccharides such as starch, dextrins, cellulose and glycogen. In another embodiment, the at least one additional sugar is chosen from any aldoses and ketoses. Further, the at least one additional sugar may be substituted or unsubstituted.

According to the present invention, the at least one additional sugar is present in the composition in an amount generally ranging from 0.01% to 10% by weight relative to the total weight of the composition, such as from 0.1% to 5% by weight.

The compositions of the present invention as well as those used in the methods of the present invention may be in the form of a liquid, an oil, a paste, a stick, a dispersion, an emulsion, a lotion, a gel, or a cream. The inventive compositions may further comprise at least one solvent. Non-limiting examples of the at least one solvent include water and organic solvents. A non-limiting example of organic solvents includes ethanol.

Further, these compositions may further comprise at least one suitable additive chosen from additives commonly used in compositions for keratinous fibers. Non-limiting examples of the at least one suitable additive include anionic surfactants, cationic surfactants, nonionic surfactants, amphoteric surfactants, fragrances, penetrating agents, antioxidants, sequestering agents, opacifying agents, solubilizing agents, emollients, colorants, screening agents (such as sunscreens and UV filters), preserving agents, proteins, vitamins, silicones, polymers such as thickening polymers, plant oils, mineral oils, synthetic oils and any other additive conventionally used in compositions for the care and/or treatment of keratinous fibers.

Needless to say, a person skilled in the art will take care to select the at least one suitable additive such that the advantageous properties of the composition in accordance with the invention are not, or are not substantially, adversely affected by the addition(s) envisaged.

The compositions of the present invention and those used in the methods of the present invention may also be provided as one-part compositions comprising at least one compound comprising at least two quaternary ammonium groups; and at least one compound comprising at least one $C_5$ to $C_7$ saccharide unit substituted with at least one amino group, and, optionally, at least one additional sugar, or in the form of a multi-component treatment or kit. The skilled artisan, based on the stability of the composition and the application envisaged, will be able to determine how the composition and/or multicomponent compositions should be stored and mixed. For example, simple sugars such as $C_5$ to $C_7$ monosaccharides are known to be stable at pH levels ranging from 4 to 9. In compositions where the pH range is below or above these levels, the sugars would be stored separately and added to the composition only at the time of application.

Thus, the present invention also relates to a kit for caring for, treating or durably conditioning at least one keratinous fiber comprising at least two compartments, wherein a first compartment comprises a first composition comprising at least one compound comprising at least two quaternary ammonium groups; and wherein a second compartment comprises a second composition comprising at least one compound comprising at least one $C_5$ to $C_7$ saccharide unit substituted with at least one amino group. In one embodiment, at least one composition further comprises at least one additional sugar, different from the at least one compound comprising at least one $C_5$ to $C_7$ saccharide unit substituted with at least one amino group.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contains certain errors necessarily resulting from the standard deviation found in their respective testing measurements. The following example is intended to illustrate the invention without limiting the scope as a result.

EXAMPLE

Durability of Polyquaternium-10 and Glucosamine

The protocol used for the determination of the heat activated durable conditioning is as follows: bleached hair was treated with an aqueous solution containing 0.5% (0.4 g solution/hair) of polyquaternium-10 (a compound comprising at least two quaternary ammonium groups) or 0.5% polyquaternium-10 and 0.5% glucosamine hydrochloride (a compound comprising at least one $C_5$ to $C_7$ saccharide unit substituted with at least one amino group) for 3 minutes then blotted dry. The treated hair was heated with a flat curling iron for 1 minute then shampooed six times with a 10% SLES solution.

The force needed to comb the wet hair was determined after the treatment and heat, and after the shampoo cycle. EaGh data point represents the average of a duplicate experiment. The results are shown in Table 1.

The % Increase in Wet Combing Work was calculated as follows:

% Increase=$[(W_f/W_i)/W_i] \times 100$ wherein:

$W_i$=Wet Combing Work Before Treatment $W_f$=Wet Combing Work After Application and Heat; or Wet Combing Work After Six Shampoos Following Application and Heat A negative % Increase indicates a better combability after treatment compared to non-treated hair.

TABLE 1

Percent Increase in Wet Combing Force of Hair Treated with Polyquaternium-10 or Polyquaternium-10 and Glucosamine Hydrochloride

| Solution | Wet Combing Work After Application and Heat Treatment (gm-in) | Wet Combing Work After Shampooing Six Times Following Application and Heat Treatment (gm-in) |
|---|---|---|
| 0.5% Polyquaternium-10 | −77.55 | 7.49 |
| 0.5% Polyquaternium-10 + 0.5% Glucosamine hydrochloride | −85.01 | −64.79 |

The data showed that the conditioning effect of polyquaternium-10 was further improved in the presence of Xyliance. Further, the work required to comb the treated hair when wet remained lower than that required to comb hair treated with polyquaternium-10 even after shampooing the hair six times. Therefore, the application of glucosamine hydrochloride and polyquaternium-10 followed by heating the hair resulted in durable conditioning of the hair.

What is claimed is:

1. A composition for durable conditioning of at least one keratinous fiber comprising:
    (a) at least one compound comprising at least two quaternary ammonium groups; and
    (b) at least one compound comprising at least one $C_5$ to $C_7$ saccharide unit substituted with at least one amino group, wherein said at least one compound comprising at least two quaternary ammonium groups and at least one compound comprising at least one $C_5$ to $C_7$ saccharide unit substituted with at least one amino group are present in an amount effective to durably condition said at least one keratinous fiber,
    with the proviso that if the at least one compound comprising at least one $C_5$ to $C_7$ saccharide unit is chosen from polysaccharides, then the amino groups are unsubstituted.

2. A composition according to claim 1, wherein said at least two quaternary ammonium groups, which may be identical or different, are each chosen from ammonium groups which are quaternized and amine groups which are capable of being quaternized.

3. A composition according to claim 2, wherein said amine groups which are capable of being quaternized are chosen from primary amine groups, secondary amine groups, and tertiary amine groups.

4. A composition according to claim 1, wherein said at least two quaternary ammonium groups, which may be identical or different, are each chosen from substituent ammonium groups which are quaternized, substituent amino groups capable of being quaternized, ammonium groups which are quaternized which form part of the skeleton of said at least one compound and amino groups capable of being quaternized which form part of the skeleton of said at least one compound.

5. A composition according to claim 1, wherein said at least one compound comprising at least two quaternary ammonium groups is chosen from:
    polymers comprising at least two quaternary ammonium groups derived from (i) at least one monomer unit comprising at least two quaternary ammonium groups as defined below and optionally (ii) at least one additional monomer unit different from said at least one monomer (i); and
    polymers comprising at least two quaternary ammonium groups derived from (i) at least one monomer comprising at least one quaternary ammonium group as defined herein and optionally (ii) at least one additional monomer unit.

6. A composition according to claim 5, wherein said at least one compound comprising at least two quaternary ammonium groups is chosen from:
    polymers comprising at least two quaternary ammonium groups derived from at least one vinyl monomer;
    cationic diallyl quaternary ammonium polymers comprising at least two quaternary ammonium groups;
    polysaccharide polymers comprising at least two quaternary ammonium groups; and
    silicone polymers comprising at least two quaternary ammonium groups.

7. A composition according to claim 6, wherein said at least one compound comprising at least two quaternary ammonium groups is chosen from:
    polymers comprising at least two quaternary ammonium groups derived from at least one vinyl monomer substituted with at least one group chosen from dialkylaminoalkyl acrylate, dialkylaminoalkyl methacrylate, monoalkylaminoalkyl acrylate, monoalkylaminoalkyl methacrylate, trialkyl methacryloxyalkyl ammonium salts, trialkyl acryloxyalkyl ammonium salts and diallyl quaternary ammonium salts;
    polymers comprising at least two quaternary ammonium groups derived from at least one vinyl quaternary ammonium monomer comprising at least one cyclic cationic nitrogen-containing ring;
    copolymers comprising at least two quaternary ammonium groups derived from (i) at least one vinyl monomer comprising at least one quaternary ammonium group and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol;
    cationic cellulose comprising at least two quaternary ammonium groups;
    cationic starch comprising at least two quaternary ammonium groups;
    cationic guar gum comprising at least two quaternary ammonium groups; and
    cellulose ethers comprising at least two quaternary ammonium groups.

8. A composition according to claim 7, wherein said at least one compound comprising at least two quaternary ammonium groups is chosen from polyquaternium-16; polyquaternium-11; quaternized poly(vinylamine); quaternized poly-4-vinyl pyridine; quaternized poly(ethyleneimine); polyquaternium-6; polyquaternium-7; polyquaternium-22; polyquaternium-39; polyquaternium-10; polyquaternium-24; quaternized starch; and amodimethicone.

9. A composition according to claim 7, wherein said at least one compound comprising at least two quaternary ammonium groups is polyquaternium-10.

10. A composition according to claim 7, wherein said at least one compound comprising at least two quaternary ammonium groups is polyquatemlurn-22.

11. A composition according to claim 7, wherein said at least one compound comprising at least two quaternary ammonium groups is quaternized starch.

12. A composition according to claim 1, wherein said at least one compound comprising at least two quaternary ammonium groups further comprises at least one counterion.

13. A composition according to claim 1, wherein said at least one compound comprising at least two quaternary ammonium groups is present in an amount ranging from 0.01% to 10% by weight relative to the total weight of the composition.

14. A composition according to claim 13, wherein said at least one compound comprising at least two quaternary ammonium groups is present in an amount ranging from 0.1% to 5% by weight relative to the total weight of the composition.

15. A composition according to claim 1, wherein said at least one amino group is chosen from unsubstituted amino groups and substituted amino groups.

16. A composition according to claim 1, wherein said at least one $C_5$ to $C_7$ saccharide unit is further substituted with at least one group different from said at least one amino group.

17. A composition according to claim 1, wherein said at least one $C_5$ to $C_7$ saccharide unit is substituted with said at least one amino group at C1 of said saccharide unit.

18. A composition according to claim 1, wherein said at least one $C_5$ to $C_7$ saccharide unit is substituted with said at least one amino group at C2 of said saccharide unit.

19. A composition according to claim 1, wherein said at least one compound comprising at least one $C_5$ to $C_7$ saccharide unit substituted with at least one amino group is chosen from $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group.

20. A composition according to claim 19, wherein said $C_5$ monosaccharides substituted with at least one amino group are chosen from pentosamines.

21. A composition according to claim 20, wherein said pentosamines are chosen from aldopentosamines and ketopentosamines.

22. A composition according to claim 21, wherein said pentosamines are chosen from xylosamine, arabinosamine, lyxosamine, ribosamine, ribulosamine and xylulosamine.

23. A composition according to claim 19, wherein said $C_6$ monosaccharides substituted with at least one amino group are chosen from hexosamines.

24. A composition according to claim 23, wherein said hexosamines are chosen from aldohexosamines and ketohexosamines.

25. A composition according to claim 24, wherein hexosamines are chosen from glucosamine, galactosamine, allosamine, altrosamine, mannosamine, gulosamine, idosamine, galactosamine, and talosamine.

26. A composition according to claim 19, wherein said $C_7$ monosaccharides substituted with at least one amino group are chosen from heptosamines.

27. A composition according to claim 26, wherein said heptosamines are chosen from aldoheptosamines and ketoheptosamines.

28. A composition according to claim 1, wherein said at least one compound comprising at least one $C_5$ to $C_7$ saccharide unit substituted with at least one amino group is chosen from oligosaccharides derived from said at least one $C_5$ to $C_7$ saccharide unit substituted with at least one amino group.

29. A composition according to claim 1, wherein said at least one $C_5$ to $C_7$ saccharide unit is chosen from furanoses.

30. A composition according to claim 1, wherein said at least one compound comprising at least one $C_5$ to $C_7$ saccharide unit substituted with at least one amino group is chosen from lyxosylamine.

31. A composition according to claim 1, wherein said at least one compound comprising at least one $C_5$ to $C_7$ saccharide unit substituted with at least one amino group is chosen from glucosamine.

32. A composition according to claim 1, wherein said at least one compound comprising at least one $C_5$ to $C_7$ saccharide unit substituted with at least one amino group is chosen from galactosamine.

33. A composition according to claim 1, wherein said at least one compound comprising at least one $C_5$ to $C_7$ saccharide unit substituted with at least one amino group is present in said composition in an amount ranging from 0.01% to 10% by weight relative to the total weight of the composition.

34. A composition according to claim 33, wherein said at least one compound comprising at least one $C_5$ to $C_7$ saccharide unit substituted with at least one amino group is present in said composition in an amount ranging from 0.1% to 5% by weight relative to the total weight of the composition.

35. A composition according to claim 1, wherein said composition further comprises at least one additional sugar, said at least one additional sugar being different from said at least one compound comprising at least one $C_5$ to $C_7$ saccharide unit substituted with at least one amino group.

36. A composition according to claim 35, wherein said at least one additional sugar is chosen from monosaccharides, oligosaccharides and polysaccharides.

37. A composition according to claim 36, wherein said monosaccharides are chosen from hexoses.

38. A composition according to claim 37, wherein said hexoses are chosen from allose, altrose, glucose, mannose, gulose, idose, galactose, talose, sorbose, psicose, fructose, and tagatose.

39. A composition according to claim 35, wherein said at least one additional sugar is present in said composition in an amount ranging from 0.01% to 10% by weight relative to the total weight of the composition.

40. A composition according to claim 39, wherein said at least one additional sugar is present in said composition in an amount ranging from 0.1% to 5% by weight relative to the total weight of the composition.

41. A composition according to claim 1, wherein said composition is in the form of a liquid, oil, paste, stick, dispersion, emulsion, lotion, gel, or cream.

42. A composition according to claim 1, wherein said at least one keratinous fiber is hair.

43. A composition according to claim 1, further comprising at least one suitable additive chosen from anionic surfactants, cationic surfactants, nonionic surfactants, amphoteric surfactants, fragrances, penetrating agents, antioxidants, sequestering agents, opacifying agents, solubilizing agents, emollients, colorants, screening agents, preserving agents, proteins, vitamins, silicones, polymers, plant oils, mineral oils, and synthetic oils.

44. A composition according to claim 1, wherein said composition is heat-activated.

45. A method for caring for or treating at least one keratinous fiber comprising:
applying to said at least one keratinous fiber a composition comprising:
(a) at least one compound comprising at least two quaternary ammonium groups; and
(b) at least one compound comprising at least one $C_5$ to $C_7$ saccharide unit substituted with at least one amino group; and
heating said at least one keratinous fiber,
wherein said at least one compound comprising at least two quaternary ammonium groups and at least one compound comprising at least one $C_5$ to $C_7$ saccharide unit substituted with at least one amino group are present in an amount effective to care for or treat said at least one keratinous fiber, with the proviso that if the at least one compound comprising at least one $C_5$ to $C_7$ saccharide unit is chosen from polysaccharides, then the amino groups are unsubstituted, and further wherein said composition is applied prior to or during said heating.

46. A method according to claim 45, further comprising wetting said at least one keratinous fiber with water prior to said application.

47. A method according to claim 45, further comprising shampooing said at least one keratinous fiber subsequent to said heating.

48. A method according to claim 47, further comprising rinsing said at least one keratinous fiber subsequent to said shampooing.

49. A method according to claim 45, wherein said at least two quaternary ammonium groups, which may be identical or different, are each chosen from ammonium groups which are quaternized and amine groups which are capable of being quaternized.

50. A method according to claim 49, wherein said amine groups which are capable of being quaternized are chosen from primary amine groups, secondary amine groups, and tertiary amine groups.

51. A method according to claim 45, wherein said at least two quaternary ammonium groups, which may be identical or different, are each chosen from substituent ammonium groups which are quaternized, substituent amino groups capable of being quaternized, ammonium groups which are quaternized which form part of the skeleton of said at least one compound and amino groups capable of being quaternized which form part of the skeleton of said at least one compound.

52. A method according to claim 45, wherein said at least one compound comprising at least two quaternary ammonium groups is chosen from:
polymers comprising at least two quaternary ammonium groups derived from (i) at least one monomer unit comprising at least two quaternary ammonium groups as defined below and optionally (ii) at least one additional monomer unit different from said at least one monomer (i); and
polymers comprising at least two quaternary ammonium groups derived from (i) at least one monomer comprising at least one quaternary ammonium group as defined herein and optionally (ii) at least one additional monomer unit.

53. A method according to claim 52, wherein said at least one compound comprising at least two quaternary ammonium groups is chosen from;
polymers comprising at least two quaternary ammonium groups derived from at least one vinyl monomer;
cationic diallyl quaternary ammonium polymers comprising at least two quaternary ammonium groups;
polysaccharide polymers comprising at least two quaternary ammonium groups; and
silicone polymers comprising at least two quaternary ammonium groups.

54. A method according to claim 53, wherein said at least one compound comprising at least two quaternary ammonium groups is chosen from:
polymers comprising at least two quaternary ammonium groups derived from at least one vinyl monomer substituted with at least one group chosen from dialkylaminoalkyl acrylate dialkylaminoalkyl methacrylate, monoalkylaminoalkyl acrylate, monoalkylaminoalkyl methacrylate, trialkyl methacryloxyalkyl ammonium salts, trialkyl acryloxyalkyl ammonium salts and diallyl quaternary ammonium salts;
polymers comprising at least two quaternary ammonium groups derived from at least one vinyl quaternary ammonium monomer comprising at least one cyclic cationic nitrogen-containing ring;
copolymers comprising at least two quaternary ammonium groups derived from (i) at least one vinyl monomer comprising at least one quaternary ammonium group and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol;
cationic tellulose comprising at least two quaternary ammonium groups;
cationic starches comprising at least two quaternary ammonium groups;
cationic guar gums comprising at least two quaternary ammonium groups; and
cellulose ethers comprising at least two quaternary ammonium groups.

55. A method according to claim 54, wherein said at least one compound comprising at least two quaternary ammonium groups is chosen from polyquaternium-16; polyquaternium-11; quaternized poly(vinylamine); quaternized poly4-vinyl pyridine; quaternized poly(ethyleneimine); polyquaternium-6; polyquaternium-7; polyquaternium-22; polyquaternium-39; polyquaternium-10; polyquaternium-24; quaternized starch; and amodimethicone.

56. A method according to claim 55, wherein said at least one compound comprising at least two quaternary ammonium groups is polyquaternium-10.

57. A method according to claim 55, wherein said at least one compound comprising at least two quaternary ammonium groups is polyquaternium-22.

58. A method according to claim 55, wherein said at least one compound comprising at least two quaternary ammonium groups is quaternized starch.

59. A method according to claim 45, wherein said at least one compound comprising at least two quaternary ammonium groups further comprises at least one counterion.

60. A method according to claim 45, wherein said at least one compound comprising at least two quaternary ammonium groups is present in an amount ranging from 0.01% to 10% by weight relative to the total weight of the composition.

61. A method according to claim 60, wherein said at least one compound comprising at least two quaternary ammonium groups is present in an amount ranging from 0.1% to 5% by weight relative to the total weight of the composition.

62. A method according to claim 45, wherein said at least one amino group is chosen from unsubstituted amino groups and substituted amino groups.

63. A method according to claim 45, wherein said at least one $C_5$ to $C_7$ saccharide unit is further substituted with at least one group different from said at least one amino group.

64. A method according to claim 45, wherein said at least one $C_5$ to $C_7$ saccharide unit is substituted with said at least one amino group at C1 of said saccharide unit.

65. A method according to claim 45, wherein said at least one $C_5$ to $C_7$ saccharide unit is substituted with said at least one amino group at C2 of said saccharide unit.

66. A method according to claim 45, wherein said at least one compound comprising at least one $C_5$ to $C_7$ saccharide unit substituted with at least one amino group is chosen from $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group.

67. A method according to claim 66, wherein said $C_5$ monosaccharides substituted with at least one amino group are chosen from pentosamines.

68. A method according to claim 67, wherein said pentosamines are chosen from aldopentosamines and ketopentosamines.

69. A method according to claim 68, wherein said pentosamines are chosen from xylosamine, arabinosamine, lyxosamine, ribosamine, ribulosamine and xylulosamine.

70. A method according to claim 66, wherein said $C_6$ monosaccharides substituted with at least one amino group are chosen from hexosamines.

71. A method according to claim 70, wherein said hexosamines are chosen from aldohexosamines and ketohexosamines.

72. A method according to claim 71, wherein hexosamines are chosen from glucosamine, galactosamine, allosamine, altrosamine, mannosamine, gulosamine, idosamine, galactosamine, and talosamine.

73. A method according to claim 66, wherein said $C_7$ monosaccharides substituted with at least one amino group are chosen from heptosamines.

74. A method according to claim 73, wherein said heptosamines are chosen from aldoheptosamines and ketoheptosamines.

75. A method according to claim 45, wherein said at least one compound comprising at least one $C_5$ to $C_7$ saccharide unit substituted with at least one amino group is chosen from oligosaccharides derived from said at least one $C_5$ to $C_7$ saccharide unit substituted with at least one amino group.

76. A method according to claim 45, wherein said at least one $C_5$ to $C_7$ saccharide unit is chosen from furanoses.

77. A method according to claim 45, wherein said at least one compound comprising at least one $C_5$ to $C_7$ saccharide unit substituted with at least one amino group is chosen from lyxosylamine.

78. A method according to claim 45, wherein said at least one compound comprising at least one $C_5$ to $C_7$ saccharide unit substituted with at least one amino group is chosen from glucosamine.

79. A method according to claim 45, wherein said at least one compound comprising at least one $C_5$ to $C_7$ saccharide unit substituted with at least one amino group is chosen from galactosamine.

80. A method according to claim 45, wherein said at least one compound comprising at least one $C_5$ to $C_7$ saccharide unit substituted with at least one amino group is present in said composition in an amount ranging from 0.01% to 10% by weight relative to the total weight of the composition.

81. A method according to claim 80, wherein said at least one compound comprising at least one $C_5$ to $C_7$ saccharide unit substituted with at least one amino group is present in said composition in an amount ranging from 0.1% to 5% by weight relative to the total weight of the composition.

82. A method according to claim 45, wherein said composition further comprises at least one additional sugar, said at least one additional sugar being different from said at least one compound comprising at least one $C_5$ to $C_7$ saccharide unit substituted with at least one amino group.

83. A method according to claim 82, wherein said at least one additional sugar is chosen from monosaccharides, oligosaccharides and polysaccharides.

84. A method according to claim 83, wherein said monosaccharides are chosen from hexoses.

85. A method according to claim 84, wherein said hexoses are chosen from allose, altrose, glucose, mannose, gulose, idose, galactose, talose, sorbose, psicose, fructose, and tagatose.

86. A method according to claim 82, wherein said at least one additional sugar is present in said composition in an amount ranging from 0.01% to 10% by weight relative to the total weight of the composition.

87. A method according to claim 86, wherein said at least one additional sugar is present in said composition in an amount ranging from 0.1% to 5% by weight relative to the total weight of the composition.

88. A method according to claim 45, wherein said composition is in the form of a liquid, oil, paste, stick, dispersion, emulsion, lotion, gel, or cream.

89. A method according to claim 45, wherein said keratinous fiber is hair.

90. A method according to claim 45, wherein said composition further comprises at least one suitable additive chosen from anionic surfactants, cationic surfactants, nonionic surfactants, amphoteric surfactants, fragrances, penetrating agents, antioxidants, sequestering agents, opacifying agents, solubilizing agents, emollients, colorants, screening agents, preserving agents, proteins, vitamins, silicones, polymers, plant oils, mineral oils, and synthetic oils.

91. The method according to claim 45, wherein said composition is applied prior to and during said heating.

92. A method for durably conditioning at least one keratinous fiber comprising: applying to said at least one keratinous fiber a composition comprising:
  (a) at least one compound comprising at least two quaternary ammonium groups; and
  (b) at least one compound comprising at least one $C_5$ to $C_7$ saccharide unit substituted with at least one amino group; and
heating said at least one keratinous fiber,
wherein said at least one compound comprising at least two quaternary ammonium groups and at least one compound comprising at least one $C_5$ to $C_7$ saccharide unit substituted with at least one amino group are present in an amount effective to durably condition said at least one keratinous fiber, with the proviso that if the at least one compound comprising at least one $C_5$ to $C_7$ saccharide unit is chosen from polysaccharides, then the amino groups are unsubstituted; and further wherein said composition is applied prior to or during said heating.

93. A method according to claim 92, further comprising wetting said at least one keratinous fiber with water prior to said applying.

94. A method according to claim 92, further comprising shampooing said at least one keratinous fiber subsequent to said heating.

95. A method according to claim 94, further comprising rinsing said at least one keratinous fiber subsequent to said shampooing.

96. A method according to claim 92, wherein said at least two quaternary ammonium groups, which may be identical or different, are each chosen from ammonium groups which are quaternized and amine groups which are capable of being quaternized.

97. A method according to claim 96, wherein said amine groups which are capable of being quaternized are chosen from primary amine groups, secondary amine groups, and tertiary amine groups.

98. A method according to claim 92, wherein said at least two quaternary ammonium groups, which may be identical or different, are each chosen from substituent ammonium groups which are quaternized, substituent amino groups capable of being quaternized, ammonium groups which are quaternized which form part of the skeleton of said at least one compound and amino groups capable of being quaternized which form part of the skeleton of said at least one compound.

99. A method according to claim 92, wherein said at least one compound comprising at least two quaternary ammonium groups is chosen from:

polymers comprising at least two quaternary ammonium groups derived from (i) at least one monomer unit comprising at least two quaternary ammonium groups as defined below and optionally (ii) at least one additional monomer unit different from said at least one monomer (i); and polymers comprising at least two quaternary ammonium groups derived from (i) at least one monomer comprising at least one quaternary ammonium group as defined herein and optionally (ii) at least one additional monomer unit.

100. A method according to claim 99, wherein said at least one compound comprising at least two quaternary ammonium groups is chosen from:

polymers comprising at least two quaternary ammonium groups derived from at least one vinyl monomer;

cationic diallyl quaternary ammonium polymers comprising at least two quaternary ammonium groups;

polysaccharide polymers comprising at least two quaternary ammonium groups; and silicone polymers comprising at least two quaternary ammonium groups.

101. A method according to claim 100, wherein said at least one compound comprising at least two quaternary ammonium groups is chosen from:

polymers comprising at least two quaternary ammonium groups derived from at least one vinyl monomer substituted with at least one group chosen from dialkylaminoalkyl acrylate, dialkylaminoalkyl methacrylate, monoalkylaminoalkyl acrylate, monoalkylaminoalkyl methacrylate, trialkyl methacryloxyalkyl ammonium salts, trialkyl acryloxyalkyl ammonium salts and diallyl quaternary ammonium salts;

polymers comprising at least two quaternary ammonium groups derived from at least one vinyl quaternary ammonium monomer comprising at least one cyclic cationic nitrogen-containing ring;

copolymers comprising at least two quaternary ammonium groups derived from (i) at least one vinyl monomer comprising at least one quaternary ammonium group and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol;

cationic cellulose comprising at least two quaternary ammonium groups;

cationic starches comprising at least two quaternary ammonium groups;

cationic guar gums comprising at least two quaternary ammonium groups; and cellulose ethers comprising at least two quaternary ammonium groups.

102. A method according to claim 101, wherein said at least one compound comprising at least two quaternary ammonium groups is chosen from polyquaternium-16; polyquaternium-11; quaternized poly(vinylamine); quaternized poly-4-vinyl pyridine; quaternized poly(ethyleneimine); polyquaternium-6; polyquaternium-7; polyquaternium-22; polyquaternium-39; polyquaternium-10; polyquaternium-24; quaternized starch; and amodimethicone.

103. A method according to claim 102 wherein said at least one compound comprising at least two quaternary ammonium groups is polyquaternium-10.

104. A method according to claim 102, wherein said at least one compound comprising at least two quaternary ammonium groups is polyquaternium-22.

105. A method according to claim 102, wherein said at least one compound comprising at least two quaternary ammonium groups is quaternized starch.

106. A method according to claim 92, wherein said at least one compound comprising at least two quaternary ammonium groups further comprises at least one counterion.

107. A method according to claim 92, wherein said at least one compound comprising at least two quaternary ammonium groups is present in an amount ranging from 0.01% to 10% by weight relative to the total weight of the composition.

108. A method according to claim 107, wherein said at least one compound comprising at least two quaternary ammonium groups is present in an amount ranging from 0.1% to 5% by weight relative to the total weight of the composition.

109. A method according to claim 92, wherein said at least one amino group is chosen from unsubstituted amino groups and substituted amino groups.

110. A method according to claim 92, wherein said at least one $C_5$ to $C_7$ saccharide unit is further substituted with at least one group different from said at least one amino group.

111. A method according to claim 92, wherein said at least one $C_5$ to $C_7$ saccharide unit is substituted with said at least one amino group at C1 of said saccharide unit.

112. A method according to claim 92, wherein said at least one $C_5$ to $C_7$ saccharide unit is substituted with said at least one amino group at C2 of said saccharide unit.

113. A method according to claim 92, wherein said at least one compound comprising at least one $C_5$ to $C_7$ saccharide unit substituted with at least one amino group is chosen from $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group.

114. A method according to claim 113, wherein said $C_5$ monosaccharides substituted with at least one amino group are chosen from pentosamines.

115. A method according to claim 114, wherein said pentosamines are chosen from aldopentosamines and ketopentosamines.

116. A method according to claim 115, wherein said pentosamines are chosen from xylosamine, arabinosamine, lyxosamine, ribosamine, ribulosamine and xylulosamine.

117. A method according to claim 113, wherein said $C_6$ monosaccharides substituted with at least one amino group are chosen from hexosamines.

118. A method according to claim 117, wherein said hexosamines are chosen from aldohexosamines and ketohexosamines.

119. A method according to claim 118, wherein said hexosamines are chosen from glucosamine, galactosamine, allosamine, altrosamine, mannosamine, gulosamine, idosamine, and talosamine.

120. A method according to claim 113, wherein said $C_7$ monosaccharides substituted with at least one amino group are chosen from heptosamines.

121. A method according to claim 120, wherein said heptosamines are chosen from aldoheptosamines and ketoheptosamines.

122. A method according to claim 92, wherein said at least one compound comprising at least one $C_5$ to $C_7$ saccharide unit substituted with at least one amino group is chosen from oligosaccharides derived from said at least one $C_5$ to $C_7$ saccharide unit substituted with at least one amino group.

123. A method according to claim 92, wherein said at least one $C_5$ to $C_7$ saccharide unit is chosen from furanoses and derivatives thereof.

124. A method according to claim 92, wherein said at least one compound comprising at least one $C_5$ to $C_7$ saccharide unit substituted with at least one amino group is chosen from lyxosylamine.

125. A method according to claim 92, wherein said at least one compound comprising at least one $C_5$ to $C_7$ saccharide unit substituted with at least one amino group is chosen from glucosamine.

126. A method according to claim 92, wherein said at least one compound comprising at least one $C_5$ to $C_7$ saccharide unit substituted with at least one amino group is chosen from galactosamine.

127. A method according to claim 92, wherein said at least one compound comprising at least one $C_5$ to $C_7$ saccharide unit substituted with at least one amino group is present in said composition in an amount ranging from 0.01% to 10% by weight relative to the total weight of the composition.

128. A method according to claim 127, wherein said at least one compound comprising at least one C5 to C7 saccharide unit substituted with at least one amino group is present in said composition in an amount ranging from 0.1% to 5% by weight relative to the total weight of the composition.

129. A method according to claim 92, wherein said composition further comprises at least one additional sugar, said at least one additional sugar being different from said at least one compound comprising at least one $C_5$ to $C_7$ saccharide unit substituted with at least one amino group.

130. A method according to claim 129, wherein said at least one additional sugar is chosen from monosaccharides, oligosaccharides and polysaccharides.

131. A method according to claim 130, wherein said monosaccharides are chosen from hexoses.

132. A method according to claim 131, wherein said hexoses are chosen from allose, altrose, glucose, mannose, gulose, idose, galactose, talose, sorbose, psicose, fructose, and tagatose.

133. A method according to claim 129, wherein said at least one additional sugar is present in said composition in an amount ranging from 0.01% to 10% by weight relative to the total weight of the composition.

134. A method according to claim 133, wherein said at least one additional sugar is present in said composition in an amount ranging from 0.1% to 5% by weight relative to the total weight of the composition.

135. A method according to claim 92, wherein said composition is in the form of a liquid, oil, paste, stick, dispersion, emulsion, lotion, gel, or cream.

136. A method according to claim 92, wherein said keratinous fiber is hair.

137. A method according to claim 92, wherein said composition further comprises at least one suitable additive chosen from anionic surfactants, cationic surfactants, nonionic surfactants, amphoteric surfactants, fragrances, penetrating agents, antioxidants, sequestering agents, opacifying agents, solubilizing agents, emollients, colorants, screening agents, preserving agents, proteins, vitamins, silicones, polymers, plant oils, mineral oils, and synthetic oils.

138. A method according to claim 92, wherein said composition is applied prior to and during said heating.

* * * * *

UNITED STATES PATENT AND TRADEMARK OFFICE
CERTIFICATE OF CORRECTION

PATENT NO. : 7,459,150 B2
APPLICATION NO. : 09/820858
DATED : December 2, 2008
INVENTOR(S) : Cannell et al.

It is certified that error appears in the above-identified patent and that said Letters Patent is hereby corrected as shown below:

In claim 7, column 12, line 48, "starch" should read --starches--.

In claim 7, column 12, line 50, "gum" should read --gums--.

In claim 10, column 12, line 67, "polyquatemlurn-22." should read --polyquaternium-22.--.

In claim 25, column 13, line 61, delete "galactosamine," (second occurrence).

In claim 53, column 15, line 65, "from;" should read --from:--.

In claim 54, column 16, line 13, "acrylate dialkylaminoalkyl methacrylate," should read --acrylate, dialkylaminoalkyl methacrylate,--.

In claim 54, column 16, line 32, "tellulose" should read --cellulose--.

In claim 55, column 16, lines 43-44, "poly4-vinyl" should read --poly-4-vinyl--.

In claim 72, column 17, lines 44-45, delete "galactosamine," (second occurrence).

In claim 123, column 21, lines 43-44, delete "and derivatives thereof".

In claim 128, column 22, line 11, "C5 to C7" should read --$C_5$ to $C_7$--.

Signed and Sealed this

Seventeenth Day of February, 2009

JOHN DOLL
*Acting Director of the United States Patent and Trademark Office*